(12) United States Patent
Faour et al.

(10) Patent No.: US 6,613,357 B2
(45) Date of Patent: Sep. 2, 2003

(54) OSMOTIC DEVICE CONTAINING PSEUDOEPHEDRINE AND AN H1 ANTAGONIST

(75) Inventors: Joaquina Faour, Buenos Aires (AR); Marcelo A. Ricci, Buenos Aires (AR)

(73) Assignee: Osmotica Corp., Tortola (VG)

(*) Notice: Subject to any disclaimer, the term of this patent is extended or adjusted under 35 U.S.C. 154(b) by 26 days.

(21) Appl. No.: 09/725,655

(22) Filed: Nov. 29, 2000

(65) Prior Publication Data

US 2002/0102305 A1 Aug. 1, 2002

Related U.S. Application Data

(60) Provisional application No. 60/175,878, filed on Jan. 13, 2000.

(51) Int. Cl.[7] ................................................. A61K 9/24
(52) U.S. Cl. ........................ 424/473; 424/468; 424/472; 424/474; 424/475; 424/476; 424/479; 424/482
(58) Field of Search ................................ 424/468, 472, 424/473, 474, 475, 476, 479, 482

(56) References Cited

U.S. PATENT DOCUMENTS

| | | | | |
|---|---|---|---|---|
| 5,314,697 A | * | 5/1994 | Kwan et al. | 424/480 |
| 5,837,379 A | * | 11/1998 | Chen et al. | 424/465 |
| 6,004,582 A | * | 12/1999 | Faour et al. | 424/473 |
| 6,171,618 B1 | * | 1/2001 | Johnson et al. | 424/472 |
| 6,258,816 B1 | * | 7/2001 | Singh et al. | 514/255 |
| 6,261,601 B1 | * | 7/2001 | Talwar et al. | 424/469 |
| 6,267,986 B1 | * | 7/2001 | Jain et al. | 424/472 |

FOREIGN PATENT DOCUMENTS

| WO | 01/19901 A2 | * | 3/2001 |
|---|---|---|---|

OTHER PUBLICATIONS

Nomeir et al., Influence of Food on the Oral Bioavailability of Loratadine and Pseudoephedrine from Extended–Release Tablets in Healthy Volunteers, J. Clin. Pharmacol, (1996), 36: 923–930.

Bronsky et al., Clinical Aspects of Allergic Disease . . . , J Allergy Clin Immunol, (Aug. 1995), vol. 96, 139–147.

Sussman et al., The efficacy and safety of fexofenadine HCl and pseudoephedrine, alone and in combination, in seasonal allergic rhinitis, J Allergy Clin Immunol, (1999), vol. 104, No. 1, 100–106.

Backhouse et al., Treatment of seasonal allergic rhinitis: a comparison of a combination tablet of terfenadine and pseudoephedrine with the individual ingredients, Br. J. Clin Pract., (1990), 44, 274–279.

Unavailable, Acrivastine/Pseudoephedrine for Allergic Rhinitis, Nurse Pract, (1995),20, 3:16–17.

(List continued on next page.)

*Primary Examiner*—Thurman K. Page
(74) *Attorney, Agent, or Firm*—Rick Matos; Innovar, L.L.C.

(57) ABSTRACT

The present invention provides an osmotic device containing controlled release pseudoephedrine in the core in combination with a rapid release H1 antagonist in an external coat. A wide range of H1 antagonist antihistamines, especially fexofenadine, can be used in this device. Particular embodiments of the invention provide osmotic devices having predetermined release profiles. One embodiment of the osmotic device includes an external coat that has been spray coated rather compression coated onto the device. The device with spray coated external core is smaller and easier to swallow than the similar device having a compression coated external coat. The device is useful for the treatment of respiratory congestion related disorders and allergy related disorders. The present devices provide PS and an H1 antagonist according to specific release profiles in combination with specific formulations.

37 Claims, 2 Drawing Sheets

OTHER PUBLICATIONS

Prevost et al., Comparative Study of SCH 434 and CTM–D in the Treatment of Seasonal Allergic Rhinitis, Clinical Therapeutics, (1994) vol. 16, No. 1, 50–56.

Ramaekers, et al., Acrivastie, terfenadine and diphenhydramine effects on driving performance as a function of dose and time after dosing, Eur J Clin Pharmacol (1994) 47:261–266.

Howarth et al., The Influence of Terfenadine and Pseudo–Ephedrine Alone and in Combination on Allergen–Induced Rhinitis, Int Arch Allergy Immunol (1993), 101:318–321.

Henaueer, et al., Effects of terfenadine and pseudoephedrine, alone and in combination in a nasal provacation test and in perennial rhinitis, Eur J Clin Pharmacol, (1991) 41:321–324.

Kosoglou et al., Pharmacokinetics of Loratadine and Pseudoephedrine Following Single and Multiple Doses of Once–Versus Twice–Daily Combination Tablet Formulations in Healthy Adult Males, Clinical Therapeutics, (1997) vol. 19, No. 5, 1002–1012.

Dockhorn et al., Efficacy of acrivastine with pseudoephedrine in treatment of allergic rhinitis due to ragweed, Annals of Allergy, Asthma, and Immunology, (1996) vol. 76, 204–208.

Toth, et al., Efficacy and safety relative to placebo of an oral formulation of cetirizine and sustained–release pseudoephedrine in the management of nasal congestion, Allergy, (1998) 53: 849–856.

Williams et al., Efficacy of acrivastine plus pseudoephedrine for symptomatic relief of seasonal allergic rhinitis due to mountain cedar, Annals of Allergy, Asthma, and Immunology, (1996), vol. 76: 432–438.

Alejandro Serra et al., Loratadine–pseudoephedrine in children with allergic rhinitis, a controlled double–blind trial, Br J Clin Pharmacol, (1998) 45:147–150.

Meran et al., A cross–over comparison of acrivastine, pseudoephedrine and their combination in seasonal allergic rhinitis, Rhinology, (1990), vol. 28:33–40.

Kaiser et al., Comparative Efficacy and Safety of Once–Daily Versus Twice–Daily Loratadine–Pseudoephedrine Combinations Versus Placebo in Seasonal Allergic Rhinitis, American Journal of Therapeutics, (1998), vol. 5, No. 4:245–251.

Berkowitz et al., The effectiveness of the nonsedating antihistamine loratadine plus pseudoephedrine in the symptomatic management of the common cold, Annals of Allergy, (1989), vol. 63, 336–339.

Grosclaude et al., Cetirizine and pseudoephedrine retard, given alone or in combination, in patients with seasonal allergic rhinitis, Rhinology, (1997), vol. 35, 67–73.

Zawisza et al., Evaluation of the Efficacy and Safety of the Loratadine with Pseudoephedrine, Pol Merkuriusz Lek, (1998) vol. 4, No. 20, 66–68.

Bojkowski et al., Acrivastine in Allergic Rhinitis: A Review of Clinical Experience, The Journal of International Medical Research, (1989), 17 (suppl 2):54B–68B.

Bertrand et al., Cetirizine and pseudoephedrine retard alone and in combination in the treatment of perennial allergic rhinitis: A double–blind multicentre study, Rhinology, (1996), vol. 34, 91–96.

Grossman et al., Loratadine–pseudoephedrine combination versus placebo in patients with seasonal allergic rhinitis, Ann Allergy, (1989), vol. 63, No. 4, 317–321.

Meyers, E.N., Comparative efficacy and safety of terfenadine with pseudoephedrine and terfenadine alone in allergic rhinitis, Otolaryngology–Head and Neck Surgery, (1998), vol. 118, No. 2, 253–255.

Segal et al., Safety and efficacy of terfenadine/pseudoephedrine versus clemastine/phenylpropanolamine in the treatment of seasonal allergic rhinitis, Annals of Allergy, vol. 70, No. 5, 389–394.

Corren et al., Efficacy and safety of loratadine plus pseudoephedrine in patients with seasonal allergic rhinitis and mild asthma, J.Allergy Clin Immunol. (1997), vol. 100, No. 6, 781–788.

Storms et al., SCH 434: A new antihistamine/decongestant for seasonal allergic rhinitis, J Allergy and Immunol, (1999), vol. 83, No. 6, 1083–1090.

Unavailable, Acrivastine/Pseudoephedrine (Semprex–D) for Seasonal Allergic Rhinitis, Med Lett Drugs Ther, (1994) vol. 36, 930, 78–80.

* cited by examiner

OSMOTIC DEVICE CONTAINING PSEUDOEPHEDRINE AND AN H1 ANTAGONIST

This application claims the benefit of provisional application No. 60/175,878, filed Jan. 13, 2000.

FIELD OF THE INVENTION

This invention pertains to an osmotic device containing pseudoephedrine and an H1 antagonist, or antihistamine. More particularly, it pertains to an osmotic device tablet, which provides a controlled release of pseudoephedrine and a rapid or immediate release of an H1 antagonist.

BACKGROUND OF THE INVENTION

Antihistamines, such as H1 antagonists, are used to treat seasonal allergic rhinitis (SAR); however, antihistamines do not effectively treat nasal congestion, e.g., stuffed or blocked nasal passages. Pseudoephedrine (Ps, a nasal decongestant) is widely used for the treatment of nasal congestion and other related diseases or disorders; however, it does not effectively treat SAR. Therefore, antihistamine/nasal decongestant combinations are frequently used to more effectively treat SAR.

The antihistamine and nasal decongestant can be administered in single or multiple dosage forms. Single dosage unit combination dosage forms containing a combination of Ps with an H1 antagonist, such as loratadine, cetirizine, fexofenadine, terfenadine, acrivastine or astemizole, are known. These combination tablet dosage forms generally provide a rapid release of the antihistamine and a controlled release of Ps. For example, Allegra-D™, Claritin-D™, Claritin-D™ 24-Hour, Seldane-D™ and Semprex-D™ (capsule) dosage forms are commercially available products that provide a rapid release of an H1 antagonist and a controlled or sustained release of Ps. These tablets are generally made for once- or twice-daily administration. U.S. Pat. No. 6,051,585 to Weinstein et al. discloses a combination formulation containing pseudoephedrine, with limited duration of action, and an antihistamine for treating SAR.

Applicant's note that Hoechst Marion Roussel has attempted unsuccessfully to develop sustained release osmotic device product that provides therapeutic blood plasma levels of PS and FEX over a 24 hour period.

Sussman et al. (*J. Allergy Clin. Immunol.* (1999 July), 104(1), pp. 100–106) have reported on the evaluation of the twice daily combined administration of fexofenadine and pseudoephedrine using two separate dosage forms: an immediate release form containing 60 mg of FEX and a sustained release form containing 120 mg of PS.

Fexofenadine (terfenadine carboxylate) and derivatives are known for the treatment of SAR. U.S. Pat. No. 4,254,129 to Carr et al., No. 5,375,693 to Woosley et al., No. 5,578,610 to D'Ambra, and No. 6,037,353 disclose the use of fexofenadine and related compounds in treating SAR.

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770, U.S. Pat. No. 4,008,719 to Theeuwes et al., U.S. Pat. No. 4,058,122 to Theeuwes et al., U.S. Pat. No. 4,116,241 to Theeuwes et al., U.S. Pat. No. 4,160,452 to Theeuwes, U.S. Pat. No. 4,256,108 to Theeuwes, and Argentina Patent No. 199,301, the entire disclosures of which are hereby incorporated by reference. In particular, tablet formulations for providing antihistamines are disclosed in U.S. Pat. No. 4,650,807 to Findlay et al., and U.S. Pat. No. 4,501,893 to Findlay et al., the entire disclosures of which are hereby incorporated by reference.

While conventional sustained release dosage forms, such as described above, are effective, osmotic devices such as those described by Faour et al. (U.S. Pat. No. 6,004,582), the entire disclosure of which is hereby incorporated by reference, are particularly advantageous for delivering two different dosage forms from a single osmotic device tablet. While Faour et al. disclose osmotic device formulations comprising slow release pseudoephedrine with rapid release loratadine and slow release pseudoephedrine with rapid release astemizol, they do not disclose osmotic devices that provide the specific formulations, plasma profiles or release profiles for the various different combinations claimed herein, nor osmotic devices having a drug-containing external coat that has been spray coated rather than compression coated onto the device.

SUMMARY OF THE INVENTION

In one aspect, the present invention provides an osmotic device comprising:

a core comprising a therapeutically effective amount of pseudoephedrine (PS) and at least one osmotic agent or osmopolymer, wherein the core provides a controlled release of pseudoephedrine;

a semipermeable membrane surrounding the core and having a passageway there through; and an external coat comprising a therapeutically effective amount of an H1 antagonist, wherein the external coat provides a rapid release of the H1 antagonist; wherein:
at least 67% of the pseudoephedrine is released within 23 hours, and at least 65% of the H1 antagonist is released within 40 minutes after exposure of the osmotic device to an aqueous solution.

In some embodiments, the H1 antagonist is selected from the group consisting of acrivastine, astemizol, azelastine, cetirizine, ebastine, epinastine, fexofenadine, loratadine, mizolastine, norastemizol, prometazine and terfenadine.

In other embodiments, the external coat is applied by spray coating rather than by compression coating. By spray coating rather than compression coating the external coat is thinner, and therefore a smaller osmotic device is formed.

Other embodiments include those wherein: 1) at least 75% of the H1 antagonist is released within 30 min after administration; 2) at least 75% of the H1 antagonist is released in 20 min after administration; 3) at least 75% of the H1 antagonist is released within 10 min after administration; 4) at least 75% of the H1 antagonist is released within 5 min after administration; 5) all of the H1 antagonist is released within 90 min after administration; 6) all of the H1 antagonist is released within 45 min after administration; 7) all of the H1 antagonist is released within 30 min after administration; 8) all of the H1 antagonist is released within 20 min after administration; 9) all of the H1 antagonist is released within 10 min after administration; 10) all of the H1 antagonist is released within 5 min after administration; 11) the osmotic device further comprises an inert and erodible water soluble lamina interposed the semipermeable membrane and the drug-containing outer coating; 12) the water soluble lamina comprises poly(vinylpyrrolidone)-(vinyl acetate) copolymer; 13) all of the H1 antagonist is released within 120 min after administration; and/or 14) all of the H1 antagonist is released within 180 min after administration.

Still other embodiments include those wherein: 1) 10–25% of the PS is released within 3 hours after administration; 2) 25–50% of the PS is released within 7 hours after administration; 3) 50–66% of the PS is released within 11 hours after administration; 4) 66–79% of the PS is released within 15 hours after administration; and 5) 79–100% of the PS is released within 23 hours after administration or 79–90% of the PS is released within 23 hours after administration. Generally, all of the PS is released within 24 hours min after administration.

Another embodiment includes one wherein: 1) 5–23% of the PS is released within 3 hours after administration; 2) 20–52% of the PS is released within 7 hours after administration; 3) 36–72% of the PS is released within 11 hours after administration; 4) 53–82% of the PS is released within 15 hours after administration; and 5) 67–100% of the PS is released within 23 hours after administration.

More embodiments include those wherein: 1) 8–12% of the PS is released within 3 hours after administration; 2) 25–32% of the PS is released within 7 hours after administration; 3) 42–52% of the PS is released within 11 hours after administration; 4) 55–70% of the PS is released within 15 hours after administration; and 5) at least 75% of the PS is released within 23 hours after administration or 75–100% of the PS is released within 23 hours after administration.

Even other embodiments of the invention include those wherein: 1) 9–11% of the PS is released within 3 hours; 2) 19–22% of the PS is released within 5 hours; 3) 28–31% of the PS is released within 7 hours; 4) 35–40% of the PS is released within 9 hours; 5) 45–50% of the PS is released within 11 hours; 6) 50–55% of the PS is released within 13 hours; 7) 60–65% of the PS is released within 15 hours; and 8) at least 67% of the PS is released within 23 hours after exposure to an aqueous environment.

Yet another embodiment of the invention includes one wherein: 1) 5–23% of the PS is released within 3 hours; 2) 12–38% of the PS is released within 5 hours; 3) 20–52% of the PS is released within 7 hours; 4) 28–62% of the PS is released within 9 hours; 5) 36–72% of the PS is released within 11 hours; 6) 44–77% of the PS is released within 13 hours; 7) 53–82% of the PS is released within 15 hours; and 8) at least 67% of the PS is released within 23 hours after exposure to an aqueous environment.

Still yet another embodiment of the invention includes an osmotic device wherein: 1) 5–23% of the PS is released within 3 hours; 2) 20–52% of the PS is released within 7 hours; 3) 36–72% of the PS is released within 11 hours; 4) 53–82% of the PS is released within 15 hours; and 5) at least 67% of the PS is released within 23 hours after exposure to an aqueous environment.

Yet other embodiments includes those wherein the PS is released at a zero order or pseudo-zero order rate for a period of at least 12 hours, at least 14 hours, at least 16 hours, at least 18 hours and at least 20 hours.

Another aspect of the invention provides a method of treating a respiratory congestion related disorder, such as nasal congestion, or an allergy related disorder, such as allergic rhinitis, in a mammal. The method comprises the step of administering an osmotic device, which provides a controlled release of pseudoephedrine from its core and a rapid release of an H1 antagonist from an external coat, wherein at least 75% of the H1 antagonist is released within about 40 minutes and at least about 67% of the pseudoephedrine is released within about 23 hours.

In other embodiments, the osmotic device has a pseudoephedrine release profile similar to that shown in FIG. 1 or 2.

Target therapeutic levels for the H1 antagonist are in the range of about 2 ng to about 700 ng per ml of plasma.

Target therapeutic levels for the pseudoephedrine are generally in the range of about 3 ng to about 1000 ng per ml of plasma.

The osmotic device generally delivers the H1 antagonist to the upper GI tract and the pseudoephedrine to the middle to lower GI tract.

Another aspect of the invention provides an osmotic device comprising:

(a) a core comprising a therapeutically effective amount of pseudoephedrine which is delivered at a controlled rate over a period of about 18–24 hours;

(b) a semipermeable membrane surrounding the core and a passageway through the semipermeable membrane;

(c) an inert water soluble coating surrounding the semipermeable membrane and plugging the passageway; and (d) a fexofenadine-containing water soluble coating surrounding the inert coating for delivering a therapeutically effective amount of fexofenadine at a rapid rate over a period of less than about 90 min.

Some specific embodiments of the invention also include those wherein the drug-containing water soluble coating is present in an amount of about 1–90% wt., 9–40% wt., at least about 25% wt., about 25–40% wt. or about 30–40% wt. based upon the total weight of the osmotic device.

Other features, advantages and embodiments of the invention will become apparent to those skilled in the art by the following description, accompanying examples.

BRIEF DESCRIPTION OF THE FIGS.

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Pseudoephedrine and H1 antagonist antihistamines are available from large number of commercial sources. The invention provides for the administration of pseudoephedrine and H1 antagonists in their free base, free acid, racemic, optically pure, diastereomeric and/or pharmaceutically acceptable salt forms. Suitable H1 antagonist antihistamines include, for example, first generation antihistamines, second generation antihistamines, diphenhydramine, chlorpheniramine, brompheniramine, tripolidine, promethacine, hydroxizine, pinlamine, dimenhydrinate, acrivastine, azelastine, cetirizine, ebastine, epinastine, fexofenadine, loratadine, mizolastine, norastemizol and prometazine.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the Ps or H1 antagonist. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as Remington's Pharmaceutical Sciences, 18th Ed. (Alfonso R. Gennaro, ed.; Mack Publishing Company, Easton, Pa., 1990); Remington: the Science and Practice of Pharmacy 19$^{th}$ Ed.(Lippincott, Williams & Wilkins, 1995); Handbook of Pharmaceutical Excipients, 3$^{rd}$ Ed. (Arthur H. Kibbe, ed.; Amer. Pharmaceutical Assoc., 1999); the Pharmaceutical Codex: Principles and Practice of Pharmaceutics 12$^{th}$ Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Figure 1:
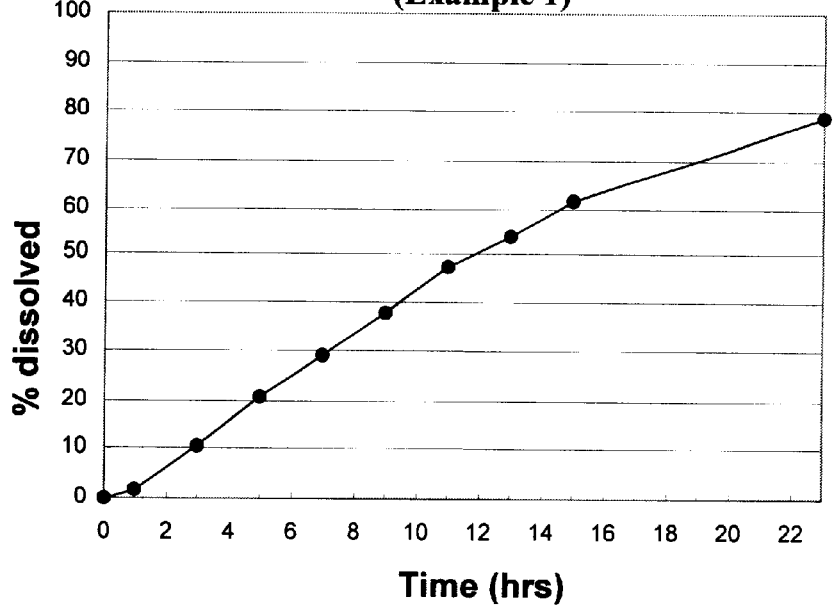
FIG. 1 depicts an in vitro dissolution profile of pseudoephedrine released from the exemplary formulation of Example 1.

FIG. 1 depicts a pseudoephedrine in vitro dissolution profile for the osmotic device tablets described in Example 1. The release profile of each osmotic device generally resembles a pseudo-zero order or first-order release profile, as seen in FIG. 1. The release profile of the osmotic device of the invention will vary from that shown in FIG. 1 according to the materials used to form the core and the semipermeable membrane covering the core. For example, the release profile can be influenced by the material used to form the semipermeable membrane covering the core, by the material used to form any coating on the semipermeable membrane, by the excipients present in the core, or by the presence of an osmagent in the core. The osmotic device of the invention can have a release profile that generally resembles a pseudo-zero order or a zero order release profile.

Depending upon the particular combination of ingredients used to prepare the osmotic device, the osmotic device will generally provide an expected overall pseudoephedrine release profile resembling a pseudo-zero order or first-zero release profile. The release profile for the formulation of Example 1 is generally described as follows, wherein the numbers in parentheses represent average values:

| Time after administration (h) | Maximum Percent Released | Minimum Percent Released |
|---|---|---|
| 1 | 2–3 (2.5) | 0.1–0.5 (0.4) |
| 3 | 11–12 (11.9) | 8–9 (8.6) |
| 5 | 22–23 (22.1) | 18–20 (18.4) |
| 7 | 30–32 (31.5) | 25–27 (26.5) |
| 9 | 40–42 (40.4) | 33–35 (34.4) |
| 11 | 50–52 (51.6) | 42–45 (44.2) |
| 13 | 55–60 (57.5) | 45–51 (49.9) |
| 15 | 65–70 (66.5) | 55–60 (57.0) |
| 23 | 75–100 (84.4) | 60–75 (72.8) |

The pseudoephedrine release profile can also be described as follows:

| Time after administration (h) | Released (%) (Avg.) |
|---|---|
| 1 | 1–2 (1.6) |
| 3 | 9–11 (10.5) |
| 5 | 19–22 (20.6) |
| 7 | 28–31 (29.2) |
| 9 | 35–40 (37.7) |
| 11 | 45–50 (47.8) |
| 13 | 50–55 (53.7) |
| 15 | 60–65 (61.7) |
| 23 | 75–80 (78.0) |

All of the tablet formulations of the invention will provide therapeutically effective levels of pseudoephedrine and an H1 antagonist for at least a predetermined period of time. The tablets of the invention will generally provide therapeutically effective amounts of pseudoephedrine for a period of not less than 18 hours and not more than 30 hours, not less than 20 hours and not more than 28 hours, not less than 18 hours and not more than 24 hours, or not less than 22 hours and not more than 24 hours.

Figure 2:
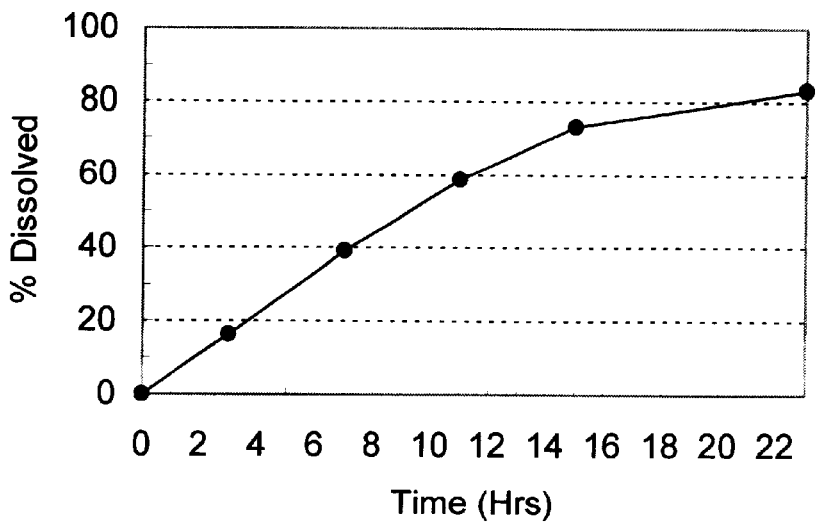
FIG. 2 depicts an in vitro dissolution profile of pseudoephedrine released from the exemplary formulation of Example 4. The data is an average of six different samples.
Figure 3:
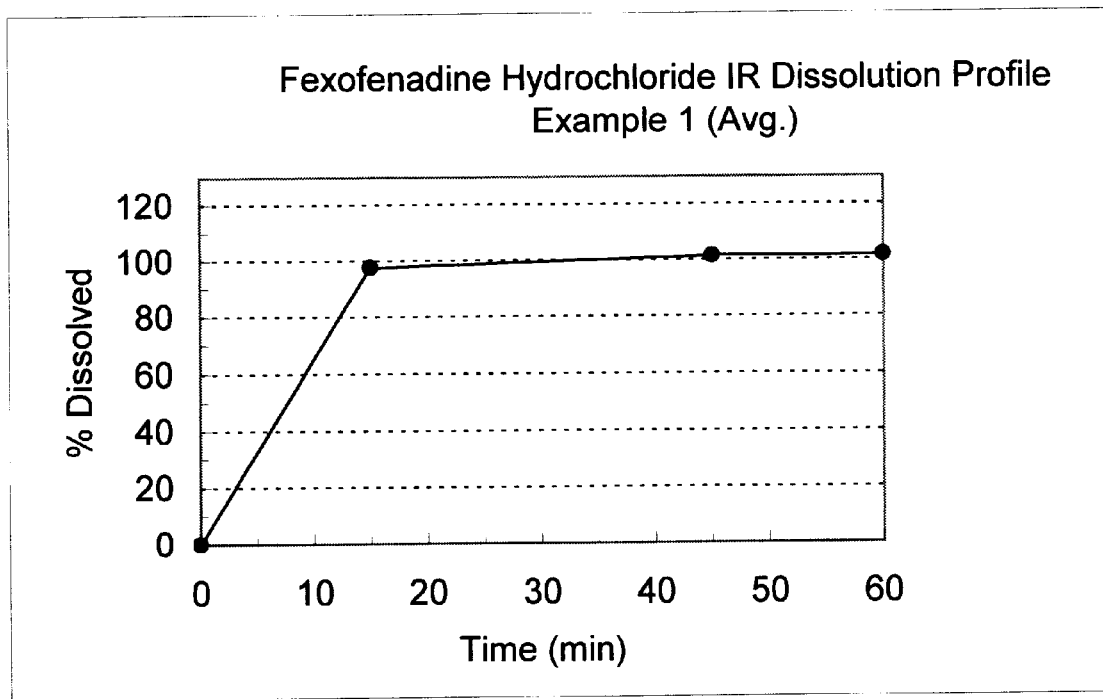
FIG. 3 depicts an in vitro release profile of fexofenadine (FEX) released from the exemplary formulation of Example 4.

The formulation of Example 4 provides a fexofenadine (FEX) dissolution profile as depicted in FIG. 3 and a PS dissolution profile as depicted in FIG. 2. The PS release profile depicted in FIG. 2 includes data from six different analyses of the formulation of Example 4. The PS release profile of FIG. 2 is generally described as follows:

| Time after administration (h) | Maximum Percent Released | Minimum Percent Released |
|---|---|---|
| 3 | 18–25 (21.6) | 8–12 (11.8) |
| 7 | 40–50 (46.6) | 30–36 (33.2) |
| 11 | 60–70 (66.4) | 48–55 (51.5) |
| 15 | 70–80 (78.3) | 60–70 (66.5) |
| 23 | 80–100 (85.3) | 70–80 (79.8) |

The pseudoephedrine release profile can also be described as follows:

| Time after administration (h) | Released (%) (Avg.) |
|---|---|
| 3 | 11–25 (16.3) |
| 7 | 25–50 (39.2) |
| 11 | 50–66 (58.7) |

-continued

| Time after administration (h) | Released (%) (Avg.) |
|---|---|
| 15 | 66–79 (73.1) |
| 23 | 79–86 (83.1) |

The external coating can be an immediately dissolving coating that dissolves in the buccal cavity or a rapidly dissolving coating that dissolves in the stomach, jejunum or duodenum. The controlled release core generally begins to release pseudoephedrine within about 0.5–3 hours or 0.5–2 hours after administration or within less than about 1 hour after administration.

The rapid release coating will release all of the H1 antagonist within three hours after administration and at least 75% of its H1 antagonist within about 40 minutes after administration. Approximately all of the FEX is released from the formulation of Example 4 in less than 20 min, or in about 15 min, as depicted in FIG. 3.

In the various formulations exemplified herein, the weight ratio of the core and the drug-containing coating with respect to the total weight of the device varies as follows.

| Example (No.) | Core (% wt.) | Drug Coating (% wt.) | Total tablet Weight (mg) |
|---|---|---|---|
| 1 | 74.5 | 9.9 | 563.1 |
| 4 | 54.1 | 35.8 | 775 |
| 5 | 61.9 | 25.8 | 677.5 |
| 6 | 74.8 | 10.7 | 560.5 |
| 7 | 55.6 | 34.1 | 755 |
| 8 | 61.5 | 26.4 | 682.5 |

Accordingly, the osmotic device of the present invention comprises a drug-containing water soluble coating present in an amount of about 9–40% wt., at least about 25% wt., about 25–40% wt. and about 30–40% wt. based upon the total weight of the osmotic device. The higher weight ranges are remarkable, since no prior art osmotic devices are known that include a sprayed drug-containing water soluble coating present in such high amounts. Also, the core is present in an amount of about 50–80% wt., about 50–75% wt., about 50–65% wt., or about 54–63% wt. based upon the total weight of the device.

The osmotic device of Example 4 (240 mg PS extended release, and 180 mg FEX immediate release) was administered to 13 healthy humans to determine the bioavailability of FEX in the osmotic device as compared to that of the Allegra® (Hoechst Marion Roussel Inc.), which is an immediate release formulation of FEX (180 mg). The bioavailability was determined by measuring blood plasma levels of FEX. The results indicate that the FEX bioavailability for the claimed product was slightly higher within the first hour and lower within the following 29 hours after administration. Overall, the area under the curve was similar for both samples tested.

Those of ordinary skill in the art will appreciate that the particular amounts of pseudoephedrine and H1 antagonist used in the osmotic device will vary according to, among other things, the desired pharmacokinetic behavior in a mammal.

A water soluble coating, inert or drug-containing, will generally comprise an inert and non-toxic material which is at least partially, and optionally substantially completely, soluble or erodible in an environment of use. Selection of materials suitable for the inert or drug-containing water soluble coatings will depend upon the desired release rate of drug from the drug-containing coating and upon the desired separation of drug delivery from the core versus the drug-containing coating. A rapidly dissolving coat will be soluble in the buccal cavity and/or upper GI tract, such as the stomach, duodenum, jejunum or upper small intestines. Exemplary materials are disclosed in U.S. Pat. No. 4,576,604 to Guittard et al. and No. 4,673,405 to Guittard et al., and No. 6,004,582 to Faour et al. and the text *Pharmaceutical Dosage Forms: Tablets Volume I, 2$^{nd}$ Edition.* (A. Lieberman. ed. 1989, Marcel Dekker, Inc.), the relevant disclosures of which are hereby incorporated by reference. In some embodiments, the rapidly dissolving coat will be soluble in saliva, gastric juices, or acidic fluids.

Materials which are suitable for making the water soluble coatings of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film forming polymers.

Other materials which can be used in the water soluble coatings include hydroxypropylcellulose, microcrystalline cellulose (MCC, Avicel.TM. from FMC Corp.), poly (ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis (methacryloyloxyethyloxycarbonylamino)-azobenzene, azopolymers, enteric coated timed release system (Time Clock® from Pharmaceutical Profiles, Ltd., UK) and calcium pectinate can be included in the water soluble coat.

The inert water soluble coat covering the semipermeable wall and blocking the passageway is made of synthetic or natural material which, through selective dissolution or erosion shall allow the passageway to be unblocked thus allowing the process of osmotic delivery to start. This slow or fast dissolving water soluble coat can be impermeable to a first external fluid, while being soluble in a second external fluid. This property can help to achieve a controlled and selective release of the active compound in the nucleus.

In some embodiments, the inert water soluble coat will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the water soluble coat. Such other polymeric materials include, by way of example and without limitation, cellulose acetate phthalate (CAP), cellulose acetate trimelletate (CAT), poly(vinyl acetate)phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit™ L-30-D (MA-EA, 1:1), Eudragit™ L-100–55 (MA-EA, 1:1), hydroxypropylmethylcellulose acetate succinate (HPMCAS), Coateric™ (PVAP), Aquateric™ (CAP), AQOAT™ (HPMCAS) and combinations thereof. The water soluble coat can also comprise dissolution aids, stability modifiers, and bioabsorption enhancers.

An optional polymeric material for use in the inert water soluble coat includes enteric materials that resist the action of gastric fluid avoiding permeation through the semipermeable wall while one or more of the materials in the core are solubilized in the intestinal tract thereby allowing delivery of a drug in the core by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The water soluble coat can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon™ K 30 has a viscosity of about 5.5–8.5 cps at 20.degree. C., and a 2% P/V aqueous solution of Methocel™ E-15 has a viscosity of about 13–18 cps at 20.degree. C.

The inert water soluble coat can also comprise other materials suitable which are substantially resistant to gastric juices and which will promote either enteric or colonic release. For this purpose, the inert water soluble coat can comprise one or more materials that do not dissolve, disintegrate, or change their structure in the stomach and during the period of time that the osmotic device resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials that form a semipermeable wall which are known by those of ordinary skill in the art of pharmaceutical sciences are suitable for this purpose. Exemplary materials are cellulose esters, cellulose ethers and cellulose esters-ethers. However, it has been found that a semipermeable membrane comprising cellulose acetate (CA) and poly(ethylene glycol) (PEG), in particular PEG 400, performs well when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and about 95% by weight of CA: about 5% by weight of PEG. The ratio can be varied to alter permeability and ultimately the release profile of the osmotic device. Other suitable materials can include a selected member of the group of cellulose acylates such as cellulose acetate, cellulose diacetate, cellulose triacetate and combinations thereof. Many suitable polymers, include those disclosed in Argentine Pat. No. 199,301, U.S. Pat. No. 6,004,582 and references cited herein, the disclosures of which are hereby incorporated by reference.

Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%; a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. No. 3,173,876, No. 3,276,586, No. 3,541,005, No. 3,541,006, and No. 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride), semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. These and others polymers are disclosed in U.S. Pat. No. 3,845,770, No. 3,916,899, No. 4,765,989 and No. 4,160,020; and in *Handbook of Common Polymers* (Scott, J. R. and Roff, W. J., eds.; 1971; CRC Press, Cleveland, Ohio).

The osmotic device of the invention comprises at least one passageway (pore, hole, or aperture) which communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. No. 4,088,864 to Theeuwes et al., No. 4,016,880 to Theeuwes et al., No. 3,916,899 to Theeuwes et al., No. 4,285,987 to Ayer et al., No. 4,783,337 to Wong et al., No. 5,558,879 to Chen et al., No. 4,801,461 to Hamel et al., and No. 3,845,770 to Theeuwes et al., the disclosures of which are hereby incorporated by reference.

The core of the osmotic device tablet of the present invention will comprise pseudoephedrine, at least one pharmaceutically acceptable excipient and optionally one or more other materials. Generally, the tablet formulations will comprise about 0.1–99.9% by weight of pseudoephedrine in the uncoated tablet core. Acceptable ranges may vary according to the desired therapeutic response, the tablet size, the amount and type of excipients used in the core of the device, the H1 antagonist used and the intended use of the osmotic device.

When the controlled release tablet is an osmotic device, osmotically effective solutes, osmotic agents or osmagents are added. These osmagents can aid in either the suspension or dissolution of the PS in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of Ps therefrom. U.S. Pat. No. 4,077,407 to Theeuwes et al., the entire disclosure of which is hereby incorporated by reference, discloses suitable osmagents.

The tablets of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide, talc and other materials known to one of ordinary skill in the art.

As used herein, the term "tablet polishing agent" is intended to mean a compound used to impart an attractive sheen to coated tablets. Such compounds include, by way of example and without limitation, carnauba wax, white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth; crospovidone and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene—maleic acid) copolymer, glycowax, castor wax, stearyl alcohol, glycerol palnitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of pseudoephedrine, or H1 antagonist, which is sufficient to elicit the required or desired therapeutic response, or in other words, the amount which is sufficient to elicit an appreciable biological response when administered to a patient.

The tablets of the invention can assume any shape or form known in the art of pharmaceutical sciences. The device of the invention can be a pill, sphere, tablet, bar, plate, paraboloid of revolution, ellipsoid of revolution or the like. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, pseudoephedrine and excipients that comprise the core are mixed in solid, semisolid or gelatinous form, then moistened and sieved through a specified screen to obtain granules. The granules are then dried in a dryer and compressed, for example, by punching to form uncoated cores. The compressed and uncoated cores are then covered with a semipermeable membrane. Subsequently, the semipermeable membrane surrounding the core should be perforated with, for example, laser equipment. Finally, an external coat containing the H1 antagonist is applied to the semipermeable membrane.

The external coat can be applied as a compression coating, but it is generally applied as a sprayed coating. The sprayed coating is thinner and lighter than the compression coating, and an osmotic device including the sprayed on external coating is, therefore, smaller than a similar osmotic device having a compression coat. Moreover, the use of a sprayed-on drug-containing water soluble coating permits the loading of higher amounts of drug than the use of a compression-coated drug-containing water soluble coating. A smaller size osmotic device generally results in increased patient compliance in taking the osmotic device and is therefore advantageous.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The advantages of the present system over known systems for administering pseudoephedrine in combination with an H1 antagonist is improved therapeutic benefit, simplified manufacturing, and increased patient compliance.

The following examples should not be considered exhaustive, but merely illustrative of only a few of the many embodiments contemplated by the present invention. The methods described herein can be followed to prepare osmotic devices according to the invention.

EXAMPLE 1

The following general method was used to prepare osmotic devices according to the invention. In one embodiment, a large scale batch of pseudoephedrine HCl (240 mg) and loratadine (10 mg) osmotic device tablets was prepared by mixing 240.00 g of pseudoephedrine HCl, 81.00 g of osmagent, 36.00 g of diluent and 50.00 g of binder. The mixture was wetted with a blend of 90.00 ml of alcohol 96° and 3.00 g of plasticizer. The blend was granulated and dried at 40–50° C. for 3 hours; then, it was screened and mixed with 2.50 g of glidant. The blend was mixed to homogeneity and 7.50 g of lubricant was added. The final blend was tabletted using biconcaves, 9.25-mm diameter punches to form uncoated cores. Core weight: 420.0 mg; hardness from 8 to 12 kp.

A first composition to cover the cores was prepared as follows: 40.85 g of Cellulose ester and 2.15 g of plasticizer was added to 495.0 ml of a blend of organic solvents. This polymer mixture was sprayed onto the tablets in a conventional pan coater to obtain film-coated tablets whose membrane coating weighed approximately 43.0 mg. A 0.50-mm hole was laser drilled through the coating in one face of the tablet.

The second coating was prepared by mixing 3.90 g of water soluble polymer, 3.50 g of opaquant, 12.58 g of Talc and 18.00 mg of colorant in Isopropyl Alcohol. This polymer mixture was sprayed onto the tablets in a conventional pan coater to obtain film-coated tablets whose membrane coating weighed approximately 20 mg.

The third coating was prepared by mixing 10.00 g of Loratadine, 30.00 g of film forming polymer, 5.40 g of plasticizer, 9.60 g of water soluble polymer (disintegrant) and 0.60 g of glidant in Purified Water. This polymer mixture was sprayed onto the tablets in a conventional pan coater to obtain film-coated tablets whose membrane coating weighed 55.6 mg approximately.

The final coating was prepared by mixing 23.46 g of film forming polymer, 1.56 g of plasticizer, 4.95 g of opaquant and 7.53 g of talc in a blend of organic solvents. This composition was sprayed onto the drug-containing coating in a conventional pan coater.

The osmagent, diluent, binder, plasticizer, glidant, disintegrant, lubricant, cellulose ester, water soluble polymer, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

The above method was used to prepare tablets having the following formulation:

| CORE (420 mg) | |
| --- | --- |
| Pseudoephedrine Hydrochloride | 240.000 mg |
| Osmagent | 80–85 mg |
| Diluent | 30–40 mg |
| Binder | 45–55 mg |
| Plasticizer | 0.5–5 mg |
| Glidant | 0.5–5 mg |
| Lubricant | 0.5–10 mg |

| COATING A (43 mg) (semipermeable membrane) | |
| --- | --- |
| Cellulose Ester | 35–45 mg |
| Plasticizer | 0.5–5 mg |

| COATING B (20 mg) (inert water soluble lamina) | |
| --- | --- |
| Water soluble polymer | 1–5 mg |
| Opaquant | 1–5 mg |
| Talc | 5–15 mg |
| Colorant | 0.01–0.5 mg |

| COATING C (55.6 mg) (drug-containing soluble lamina) | |
| --- | --- |
| Loratadine | 10.000 mg |
| Film forming polymer | 20–40 mg |
| Plasticizer | 1–10 mg |
| Disintegrant or water soluble polymer | 5–15 mg |
| Glidant | 0.1–5 mg |

| COATING D (polish coating) | |
| --- | --- |
| Film forming polymer | 10–20 mg |
| Plasticizer | 0.1–5 mg |
| Opaquant | 1–5 mg |
| Talc | 1–10 mg |

EXAMPLE 2

The following general method was used to prepare other osmotic devices according to the invention. In one embodiment, D-pseudoephedrine hydrochloride (2,400 g), osmagent (810 g), diluent (360.0 g) and binder (500 g) are mixed in a laboratory mixer. The mixture is then sieved through a 40 mesh screen and kneaded while adding of solution containing plasticizer (10.7%) in ethyl alcohol. The wet product is sieved through an 8 mesh screen and dried in a heated oven for 12 hours at 45° C. A mixture of glidant (25.0 g) and lubricant (75.0 g), previously sieved through a 50 mesh screen, is added to the dry granulate. The resulting granulate mixture is compressed in a compressor with 10 mm diameter punches to form uncoated cores.

Resulting uncoated cores are then coated with a solution containing cellulose ester (95%) and plasticizer (5%) in a blend of organic solvents to form semipermeable membrane coated cores.

The semipermeable membrane coat of each core is then perforated with laser equipment to form at least one passageway through the semipermeable coat.

The perforated cores are then covered with a suspension comprising water soluble polymer (disintegrant) (19.56%), opaquant (16.59%), glidant (62.2%), and colorant (1.66%) in organic solvent to form cores coated with an inert and erodible water soluble polymer coat.

The coated cores having sealed passageways are subjected to a coating process through compression with a granulate as follows. In a laboratory mixer-kneader, loratadine (80 g), first filler (1516.0 g), diluent (1600 g), second filler (400 g) are mixed. This wet mixture is sieved through a 40 mesh screen and later kneaded with a solution containing binder (41.18%), first plasticizer (47.06%), and second plasticizer (11.16%) in deionized water. The wet mixture is then sieved through a 10 mesh screen and dried in a heated oven at 45° C. for 12 hours. The dried granulate is sieved through a 20 mesh screen and then mixed with a previously prepared mixture of glidant (16.0 g) and lubricant (48.0 g) and the final mixture is sieved through a 50 mesh screen to form a granulate. This resulting granulate is applied over the coated core through compression, as previously described. These particular devices have a 14 mm outer diameter and containing a 10 mm outer diameter osmotic core.

Finally, a finish coat is applied to the devices by applying a suspension comprising film forming polymer (60.27%), plasticizer (17.18%), and opaquant (22.55%) in a blend of organic solvents optionally containing water.

The osmagent, diluent, binder, plasticizer, glidant, lubricant, cellulose ester, water soluble polymer (disintegrant), opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

EXAMPLE 3

D-pseudoephedrine (2,400.0 g), osmagent (810.02 g), diluent (1335.0 g) and water soluble polymer (400.0 g) are mixed in a laboratory mixer. The mixture is then sieved through a 40 mesh screen and kneaded while adding a solution containing water soluble polymer (30%) in ethyl alcohol (96% in water). The wet product is sieved through a 10 mesh screen and dried in a heated oven for 5 hours at 45° C. A mixture of glidant (29.97 g) and lubricant (75.0 g), previously sieved through a 50 mesh screen, is added to a dry granulate. The resulting granulate mixture is compressed in a compressor with 10 mm diameter punches to form uncoated cores.

Resulting uncoated cores are then coated with a solution containing cellulose ester (95%) and plasticizer (5%) in a mixture of organic solvents to form semipermeable membrane coated cores.

The semipermeable membrane coat of each core is then perforated with laser equipment to form at least one passageway through the semipermeable coat.

The perforated cores are then covered with a suspension comprising water soluble copolymer (disintegrant) (19.56%), opaquant (16.59), filler (62.2%), and colorant (1.66%) in organic solvent (25%) to form cores coated having passageways sealed with the polymer coat of the invention.

The coated cores having blocked passageways are then coated with a suspension comprising astemizol (52.00%); suspending agent (2.65%); disintegrant (15.63%); first plasticizer (1.63%); water soluble polymer (25.95%); polysorbate 20 (1.06%), and second plasticizer (1.06%) in organic solvent (4%).

A finish coat is then applied by spraying the following suspension onto the cores: film forming polymer (60.27%); plasticizer (17.18%); opaquant (21.50%); colorant (1.05%), in a mixture of organic solvents 50% first solvent/50% second solvent; followed by drying of the finish coat.

The osmagent, diluent, binder, plasticizer, glidant, lubricant, cellulose ester, water soluble polymer (disintegrant), opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

EXAMPLE 4

The procedure of Example 1 was used to prepare the following osmotic devices, except that the tablets contained the following ingredients in the amounts indicated.

| CORE | |
|---|---|
| Pseudoephedrine Hydrochloride | 240.00 mg |
| Osmagent | 70–90 mg |
| Diluent | 30–40 mg |
| Binder | 40–60 mg |
| Plasticizer | 0.5–5 mg |
| Glidant | 0.5–5 mg |
| Lubricant | 5–10 mg |

| COATING A | |
|---|---|
| Cellulose ester | 35–45 mg |
| Plasticizer | 0.5–5 mg |

| COATING B | |
|---|---|
| Water soluble polymer | 1–5 mg |
| Opaquant | 0.5–5 mg |
| Filler | 5–15 mg |
| Colorant | 0.01–0.05 mg |

| COATING C | |
|---|---|
| Fexofenadine Hydrochloride | 180.00 mg |
| Film forming polymer | 20–25 mg |
| Disintegrant | 50–70 mg |
| Plasticizer | 5–15 mg |
| Filler | 0.5–10 mg |

| COATING D | |
|---|---|
| Film forming polymer | 1–7.5 mg |
| Plasticizer | 0.5–5 mg |
| Opaquant | 1–10 mg |
| Filler | 0.1–5 mg |
| Water soluble polymer | 1–5 mg |

The osmagent, diluent, binder, plasticizer, glidant, lubricant, cellulose ester, water soluble polymer, disintegrant, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

EXAMPLE 5

The procedure of Example 1 was used to prepare the following osmotic devices, except that the tablets contained the following ingredients in the amounts indicated.

| CORE | |
|---|---|
| Pseudoephedrine Hydrochloride | 240.00 mg |
| Osmagent | 70–90 mg |
| Diluent | 30–40 mg |
| Binder | 40–60 mg |
| Plasticizer | 0.5–5 mg |
| Glidant | 0.5–5 mg |
| Lubricant | 5–10 mg |

| COATING A | |
|---|---|
| Cellulose Ester | 40–50 mg |
| Plasticizer | 1–3 mg |

| COATING B | |
|---|---|
| Water soluble polymer | 1–5 mg |
| Opaquant | 0.5–5 mg |
| Filler | 5–15 mg |
| Colorant | 0.01–0.05 mg |

| COATING C | |
|---|---|
| Fexofenadine Hydrochloride | 120.00 mg |
| Film forming polymer | 10–20 mg |
| Water soluble copolymer | 20–30 mg |
| Plasticizer | 2.5–7.5 mg |
| Disintegrant | 5–10 mg |

| COATING D | |
|---|---|
| Film forming polymer | 10–15 mg |
| Plasticizer | 2–5 mg |

-continued

| | |
|---|---|
| Opaquant | 5–10 mg |
| Filler | 0.5–5 mg |
| Disintegrant | 1–5 mg |

The osmagent, diluent, binder, plasticizer, glidant, lubricant, disintegrant, filler, cellulose ester, water soluble polymer, water soluble copolymer, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

A tablet made according to this procedure provides a PS release profile similar to the ones depicted in FIGS. 1 and 2 and an FEX release profile similar to the one depicted in FIG. 3.

EXAMPLE 6

The procedure of Example 1 was used to prepare the following osmotic devices, except that the tablets contained the following ingredients in the amounts indicated. More over, the core, Coating A and Coating B were made as described in Example 5.

| COATING C | |
|---|---|
| Epinastine Hydrochloride | 20.00 mg |
| Film forming polymer | 20–30 mg |
| Dispersant | 0.1–2 mg |
| Plasticizer | 2–8 mg |
| Disintegrant | 5–10 mg |
| COATING D | |
| Water soluble polymer | 10–15 mg |
| Plasticizer | 0.1–1 mg |
| Opaquant | 0.1–5 mg |
| Filler | 1–5 mg |
| Disintegrant | 1–5 mg |

The osmagent, diluent, binder, plasticizer, glidant, lubricant, disintegrant, filler, cellulose ester, water soluble polymer, water soluble copolymer, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

A tablet made according to this procedure provides a PS release profile similar to the ones depicted in FIGS. 1 and 2 and an epinastine release profile similar to the one depicted in FIG. 3.

EXAMPLE 7

The procedure of Example 1 was used to prepare the following osmotic devices, except that the tablets contained the following ingredients in the amounts indicated. In addition, the core, Coating A and Coating B were made according to Example 5.

| COATING C | |
|---|---|
| Fexofenadine Hydrochloride | 120.00 mg |
| Film forming polymer | 20–40 mg |
| Plasticizer | 1–7.5 mg |
| Disintegrant | 20–30 mg |
| COATING D | |
| Film forming polymer | 5–10 mg |
| Plasticizer | 1–5 mg |
| Opaquant | 5–10 mg |
| Filler | 0.1–5 mg |
| Disintegrant | 1–5 mg |

The osmagent, diluent, binder, plasticizer, glidant, lubricant, disintegrant, filler, cellulose ester, water soluble polymer, water soluble copolymer, opaquant, and film forming polymer used in the present formulation were selected from the respective groups of ingredients set forth above. The organic solvents used herein can include, for example, ethanol, methanol, isopropanol, methylene chloride, and others typically used in the pharmaceutical sciences.

A tablet made according to this procedure provides a PS release profile similar to the ones depicted in FIGS. 1 and 2 and an FEX release profile similar to the one depicted in FIG. 3.

The devices of the invention can contain 60–240 mg, 120–240 mg or 180–240 mg of pseudoephedrine as either its free-base, salt form or combination thereof.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim:

1. An osmotic device comprising:
   (a) a core comprising a therapeutically effective amount of pseudoephedrine which is delivered at a controlled rate over a period of about 18–24 hours;
   (b) a semipermeable membrane surrounding the core and a passageway through the semipermeable membrane;
   (c) an inert water soluble or erodible coating surrounding the semipermeable membrane and plugging the passageway; and
   (d) a fexofenadine-containing water soluble or erodible coating surrounding the inert water soluble coating for delivering all of the fexofenadine at a rapid rate over a period of less than about 90 min, wherein: 1) 10–25% of the PS is released within 3 hours; 2) 25–50% of the PS is released within 7 hours; 3) 50–66% of the PS is released within 11 hours; 4) 66–79% of the PS is released within 15 hours; and 5) 79–100% of the PS is released within 23 hours after exposure to an aqueous environment.

2. The osmotic device of claim 1, wherein about 60–240 mg of pseudoephedrine are present and about 60–180 mg of fexofenadine are present.

3. The osmotic device of claim 1, wherein the drug-containing water soluble or erodible coating is present in an amount of at least about 25% wt. based upon the total weight of the osmotic device.

4. The osmotic device of claim 1, wherein the drug-containing water soluble or erodible coating is present in an amount of about 25–40% wt. based upon the total weight of the osmotic device.

5. The osmotic device of claim 1, wherein the drug-containing water soluble or erodible coating is present in an amount of about 30–40% wt. based upon the total weight of the osmotic device.

6. The osmotic device of claim 1, wherein the pseudoephedrine is released at a zero-order or pseudo-zero order rate.

7. The osmotic device of claim 1, wherein all of the fexofenadine is released over a period of less than about 60 min.

8. The osmotic device of claim 1, wherein all of the fexofenadine is released over a period of less than about 45 min.

9. The osmotic device of claim 1, wherein all of the fexofenadine is released over a period of less than about 30 min.

10. The osmotic device of claim 1, wherein all of the fexofenadine is released over a period of less than about 20 min.

11. The osmotic device of claim 1, wherein all of the fexofenadine is released over a period of less than about 10 min.

12. The osmotic device of claim 2, wherein:
the core further comprises an osmagent, a diluent and a binder;
the semipermeable membrane comprises a cellulose ester and a plasticizer;
the inert water soluble or erodible coating comprises a water soluble polymer, an opaquant and a filler; and
the fexofenadine-containing water soluble or erodible coating further comprises a film forming polymer and a disintegrant.

13. The osmotic device of claim 12, wherein:
the osmagent is selected from the group consisting of sodium chloride, salt, mannitol, acid, sugar, base, calcium salt, sodium salt, and lactose;
the diluent is selected from the group consisting of microcrystalline cellulose, lactose, sucrose, mannitol, cellulose, starch, sorbitol, dibasic calcium phosphate, and calcium carbonate;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose ester is selected from the group consisting of cellulose acetate, cellulose acylate, cellulose fatty acid ester, and cellulose acetate phthalate;
the plasticizer is independently selected at each occurrence from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate;
the water soluble polymer is independently selected at each occurrence from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum;
the film forming polymer is selected from the group consisting of hydroxypropyl methylcellulose, and poly(vinylpyrrolidone);
the disintegrant is selected from the group consisting of crospovidone, bentonite clay, microcrystalline cellulose, starch, carboxymethylcellulose, alginate, sodium starch glycolate, and gum.

14. The osmotic device of claim 13, wherein:
the opaquant is selected from the group consisting of titanium dioxide and talc; and
the filler is selected from the group consisting of talc and starch.

15. The osmotic device of claim 12, wherein:
the osmagent is present in an amount ranging from 70–90 mg;
the diluent is present in an amount ranging from 30–40 mg;
the binder is present in an amount ranging from 40–60 mg;
the cellulose ester is present in an amount ranging from 35–45 mg;
the film-forming polymer in the fexofenadine-containing water soluble or erodible coating is present in an amount ranging from 20–25 mg; and
the disintegrant in the fexofenadine-containing water soluble or erodible coating is present in an amount ranging from 50–70 mg.

16. The osmotic device of claim 12, wherein:
the osmagent is present in an amount ranging from 70–90 mg;
the diluent is present in an amount ranging from 30–40 mg;
the binder is present in an amount ranging from 40–60 mg;
the cellulose ester is present in an amount ranging from 40–50 mg;
the film-forming polymer in the fexofenadine-containing water soluble or erodible coating is present in an amount ranging from 10–20 mg;
the disintegrant in the fexofenadine-containing water soluble or erodible coating is present in an amount ranging from 5–10 mg;
and the fexofenadine-containing water soluble or erodible coating further comprises a water soluble copolymer present in an amount ranging from 20–30 mg.

17. The osmotic device of claim 12, wherein:
the osmagent is present in an amount ranging from 70–90 mg;
the diluent is present in an amount ranging from 30–40 mg;
the binder is present in an amount ranging from 40–60 mg;
the cellulose ester is present in an amount ranging from 35–45 mg;
the film-forming polymer in the fexofenadine-containing water soluble or erodible coating is present in an amount ranging from 20–40 mg; and the disintegrant in the fexofenadine-containing water soluble or erodible coating is present in an amount ranging from 20–30 mg.

18. A method of treating a respiratory congestion related disorder in a mammal comprising the step of administering an osmotic device according to any one of claims 1–3, 6–7, 12–13, 15–17.

19. An osmotic device comprising:
(a) a core comprising a therapeutically effective amount of pseudoephedrine which is delivered at a controlled rate over a period of about 18–24 hours;
(b) a semipermeable membrane surrounding the core and a passageway through the semipermeable membrane;
(c) an inert water soluble or erodible coating surrounding the semipermeable membrane and plugging the passageway; and
(d) a fexofenadine-containing water soluble or erodible coating surrounding the inert water soluble coating for delivering all of the fexofenadine at a rapid rate over a period of less than about 90 min, wherein: 1) 9–11% of the PS is released within 3 hours; 2) 19–22% of the PS is released within 5 hours; 3) 28–31% of the PS is released within 7 hours;
4) 35–40% of the PS is released within 9 hours; 5) 45–50% of the PS is released within 11 hours; 6) 50–55% of the PS is released within 13 hours; 7) 60–65% of the PS is released within 15 hours; and 8) at least 75% of the PS is released within 23 hours after exposure to an aqueous environment.

20. The osmotic device of claim 19, wherein about 60–240 mg of pseudoephedrine are present and about 60–180 mg of fexofenadine are present.

21. The osmotic device of claim 19, wherein the drug-containing water soluble or erodible coating is present in an amount of at least about 25% wt. based upon the device.

22. The osmotic device of claim 19, wherein the drug-containing water soluble or erodible coating is present in an amount of about 25–40% wt. based upon the total weight of the osmotic device.

23. The osmotic device of claim 19, wherein the drug-containing water soluble or erodible coating is present in an amount of about 30–40% wt. based upon the total weight of the osmotic device.

24. The osmotic device of claim 19, wherein the pseudoephedrine is released at a zero-order or pseudo-zero order rate.

25. The osmotic device of claim 19, wherein all of the fexofenadine is released over a period of less than about 60 min.

26. The osmotic device of claim 19, wherein all of the fexofenadine is released over period of less than about 45 min.

27. The osmotic device of claim 19, wherein all of the fexofenadine is released ever a period of less than about 30 min.

28. The osmotic device of claim 19, wherein all of the fexofenadine is released over a period of less than about 20 min.

29. The osmotic device of claim 19, wherein all of the fexofenadine is released over a period of less than about 10 min.

30. The osmotic device of claim 20, wherein:
the core further comprises an osmagent, a diluent and a binder;
the semipermeable membrane comprises a cellulose ester and a plasticizer;
the inert water soluble or erodible coating comprises a water soluble polymer, an opaquant and a filler; and
the fexofenadine-containing water soluble or erodible coating further comprises a film forming polymer and a disintegrant.

31. The osmotic device of claim 30, wherein:
the osmagent is selected from the group consisting of sodium chloride, salt, mannitol, acid, sugar, base, calcium salt, sodium salt, and lactose;
the diluent is selected from the group consisting of microcrystalline cellulose, lactose, sucrose, mannitol, cellulose, starch, sorbitol, dibasic calcium phosphate, and calcium carbonate;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose ester is selected from the group consisting of cellulose acetate, cellulose acylate, cellulose fatty acid ester, and cellulose acetate phthalate;
the plasticizer is independently selected at each occurrence from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate;
the water soluble polymer is independently selected at each occurrence from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum;
the film forming polymer is selected from the group consisting of hydroxypropyl methylcellulose, and poly(vinylpyrrolidone);
the disintegrant is selected from the group consisting of crospovidone, bentonite clay, microcrystalline cellulose, starch, carboxymethyleellulose, alginate, sodium starch glycolate, and gum.

32. The osmotic device of claim 31 wherein:
the opaquant is selected from the group consisting of titanium dioxide and talc; and
the filler is selected from the group consisting of talc and starch.

33. The osmotic device of claim 30, wherein:
the osmagent is present in an amount ranging from 70–90 mg;
the diluent is present in an amount ranging from 30–40 mg;
the binder is present in an amount ranging from 40–60 mg;
the cellulose ester is present in an amount ranging from 35–45 mg;
the film-forming polymer in the fexofenadine-containing water soluble or erodible coating is present in an amount ranging from 20–25 mg; and
the disintegrant in the fexofenadine-containing water soluble or erodible coating is present in an amount ranging from 50–70 mg.

34. The osmotic device of claim 30, wherein:

the osmagent is present in an amount ranging from 70–90 mg;

the diluent is present in an amount ranging from 30–40 mg;

the binder is present in an amount ranging from 40–60 mg;

the cellulose ester is present in an amount ranging from 40–50 mg;

the film-forming polymer in the fexofenadine-containing water soluble or erodible coating is present in an amount ranging from 10–20 mg;

the disintegrant in the fexofenadine-containing water soluble or erodible coating is present in an amount ranging from 5–10 mg;

and the fexofenadine-containing water soluble or erodible coating further comprises a water soluble copolymer present in an amount ranging from 20–30 mg.

35. The osmotic device of claim 30, wherein:

the osmagent is present in an amount ranging from 70–90 mg;

the diluent is present in an amount ranging from 30–40 mg;

the binder is present in an amount ranging from 40–60 mg;

the cellulose ester is present in an amount ranging from 35–45 mg;

the film-forming polymer in the fexofenadine-containing water soluble or erodible coating is present in an amount ranging from 20–40 mg; and the disintegrant in the fexofenadine-containing water soluble or erodible coating is present in an amount ranging from 20–30 mg.

36. An osmotic device comprising:

(a) a core comprising a therapeutically effective amount of pseudoephedrine which is delivered at a controlled rate over a period of about 18–24 hours;

(b) a semipermeable membrane surrounding the core and a passageway through the semipermeable membrane;

(c) an inert water soluble or erodible coating surrounding the semipermeable membrane and plugging the passageway; and (d) a fexofenadine-containing water soluble or erodible coating surrounding the inert water soluble coating for delivering all of the fexofenadine at a rapid rate over a period of less than about 90 min, wherein: 1) 5–23% of the PS is released within 3 hours; 2) 20–52% of the PS is released within 7 hours; 3) 36–72% of the PS is released within 11 hours; 4) 53–82% of the PS is released within 15 hours; and 5) at least 75% of the PS is released within 23 hours after exposure to an aqueous environment.

37. A method of treating a respiratory congestion related disorder in a mammal rising the step of administering an osmotic device according to any one of claims 19–35 or 36.

* * * * *